United States Patent [19]

Tantram et al.

[11] Patent Number: 4,587,003

[45] Date of Patent: May 6, 1986

[54] GAS SENSOR

[75] Inventors: Anthony D. S. Tantram, Great Bookham; Yat S. Chan, London, both of England

[73] Assignee: City Technology Limited, London, England

[21] Appl. No.: 611,876

[22] Filed: May 18, 1984

[30] Foreign Application Priority Data

May 19, 1983 [GB] United Kingdom ................ 8313846

[51] Int. Cl.[4] ........................................... G01N 27/46
[52] U.S. Cl. .................................. 204/412; 204/1 T; 204/415; 204/431; 204/432
[58] Field of Search ............... 204/1 Y, 1 P, 415, 431, 204/432, 412

[56] References Cited

U.S. PATENT DOCUMENTS

| | | | |
|---|---|---|---|
| 2,898,282 | 8/1959 | Flook et al. | 204/1 Y |
| 3,208,926 | 9/1965 | Eckfeldt | 204/409 |
| 3,227,643 | 1/1966 | Oklin et al. | 204/415 |
| 3,429,796 | 2/1969 | Lauer | 204/415 |
| 3,711,395 | 1/1973 | Plank et al. | 204/415 |
| 3,776,832 | 12/1973 | Oswin et al. | 204/412 |
| 3,793,158 | 2/1974 | Hamilton | 204/1 Y |
| 3,855,096 | 12/1974 | Bergman | 204/415 |
| 3,928,162 | 12/1975 | Takata | 204/1 Y |
| 4,152,233 | 5/1979 | Chand | 204/415 |
| 4,233,031 | 11/1980 | Matson et al. | 204/412 |

*Primary Examiner*—T. Tung
*Attorney, Agent, or Firm*—Solon B. Kemon

[57] ABSTRACT

An electro-chemical cell has porous sensing and counter electrodes S, C mounted on porous PTFE tapes 4, 5 and contacting the electrolyte of the cell which is drawn from a reservoir by a wick 12. Gas passes directly to the electrode S at 14 and any gas which does not react passes through the electrode S to the electrode C, passing across the electrolyte space by way of a porous insulating separator 10 which is partly hydrophilic and partly hydrophobic, thus providing a path for gas while preserving the electrolyte path between the electrodes. The current flowing between the electrodes is measured in the usual way. The electrode C will not see any particular gas which reacts fully at the electrode S since it will be removed by this electrode first. The electrode C will, however, see any other gas which only partially reacts at the electrode S, thus achieving partial or even complete elimination of the effect of an interfering gas.

15 Claims, 8 Drawing Figures

GAS SENSOR

This application is related to Ser. No. 631,832, filed on even date herewith, and now abandoned.

This invention relates to electro-chemical gas sensors in which the gas or vapour to be sensed is caused to react at an electrode of an electro-chemical cell to generate a current which is a function of the concentration of the gas or vapour to be sensed.

There is an increasing demand for gas sensors for safety monitoring, pollution control, fire detection, flue gas analysis, process control and so forth. In many cases, particularly for safety monitoring concerned with toxic gases where the safe limits are in the low ppm range, a high level of discrimination is required and it is important to reduce the effect of any interferences with the signal as far as possible.

A problem encountered with many electro-chemical gas sensors is that they are not completely specific. In some cases an interfering gas will give a full signal at the electrode eposed to the gas, i.e. it will be fully reacted at this electrode. In other cases there is only partial reaction so that there is a residual finite partial pressure of the interfering gas at this electrode.

According to the invention a gas sensor comprising an electro-chemical cell has first and second electrodes contacting the electrolyte of the cell arranged in such a way that gas access is provided directly to the first electrode and to the second electrode via the first electrode, and means for measuring the current passing between the first and second electrodes. The second electrode will not see any particular gas which reacts fully at the first electrode since it will be removed by this electrode first. The second electrode will, however, see any other gas which only partially reacts at the first electrode. For this reason it is possible to achieve partial or even complete elimination of the effect of the interfering gas as described below.

Since both electrodes are in contact with the electrolyte of the cell, the access of the gas under test to the second electrode must not hinder the access of electrolyte to that electrode. To facilitate this, the arrangement of electrodes is preferably such that the gas passes through the first electrode before reaching the second electrode, rather than passing around it, which is the alternative. The requirement is thus to provide parallel but separate paths for the electrolyte and the gas between the two electrodes, and this is preferably achieved by means of a porous insulating separator which is partly hydrophilic and partly hydrophobic. The hydrophobic parts of the separator provide a path for gas while preserving a path for the electrolyte through the hydrophilic parts. Such a separator is used in conjunction with a hydrophobic electrode of a known fuel cell type, that is to say comprising a network of catalyst particle aggregates, which are hydrophilic and will wet up with electrolyte, interleaved with a network of porous PTFE, which is hydrophobic and will remain unwetted so providing gas paths throughout the depth of the electrode. Such electrodes are permeable to gas even when wetted with electrolyte. Such an electrode may be pressure bonded to a porous PTFE tape.

It has been found, for example, that with a simple two electrode sensor of the fuel cell type (as just described) designed for the measurement of carbon monoxide in air and using platinum electrodes the provision of gas access to the counter electrode via the sensing electrode by means of a separator of the kind just described, substantially decreases the cross interference from hydrogen. In this sensor the nominal reactions are, at the sensing electrode, $$CO + H_2O = CO_2 + 2H^+ + 2e$$

and, at the counter electrode, $$\tfrac{1}{2}O_2 + 2H^+ + 2e = H_2O.$$

The electrodes may be connected with a simple load resistor to enable a voltage signal, equal to $iR_L$ where $i$ is the current and $R_L$ the value of the load resistor, to be taken off, which is a measure of the CO concentration. Hydrogen will give a partial interference signal with a normal sensor of this type.

In such a sensor all the CO reacts at the sensing electrode but transmission of hydrogen via the sensing electrode to the counter electrode will lower the potential of the counter electrode, which in turn will pull down the potential of the sensing electrode since it is coupled via the load resistor and so reduce the current flowing which will offset the increase in current due to partial hydrogen reaction at the sensing electrode.

By the inclusion of an additional third electrode without gas access and spaced from the second electrode within the electrolyte and means for measuring the current passing between the first electrode and the third electrode and/or the current passing between the second electrode and the third electrode, it is possible to filter out an interfering gas, i.e. an extraneous gas which interferes with the measurement of the gas of primary interest, and obtain signals corresponding to both the interfering gas and the gas of primary interest. The first electrode, i.e. that with primary access to the gas is chosen so that, by virtue of its catalytic material and/or the potential at which it is controlled, it will fully react with the interfering gas but only partially or not at all with the gas of primary interest. Accordingly, the interfering gas fully reacts at the first electrode and does not pass on to the second electrode at all. The gas of primary interest, however, will pass to, and react at, the second electrode so that the current between the second electrode and the third electrode which passes through the electrolyte in the usual way, provides a measure of the gas of primary interest.

A reference electrode may be included which is connected to a potentiostatic circuit to control the potential of either the first or the second electrode. If required, two separate potentiostatic circuits may be used to independently control the potentials of both the first and the second electrodes.

The invention will now be described in more detail, with reference to the accompanying drawings, in which.

Figure 1:
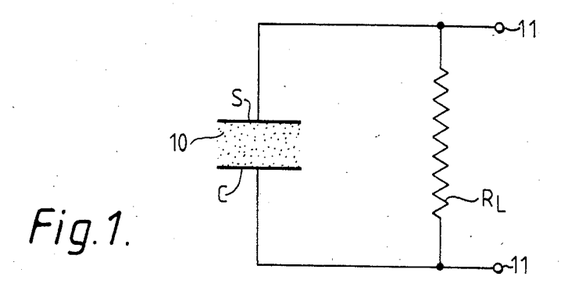
FIG. 1 is an explanatory circuit diagram.

FIG. 1 is a simple circuit diagram illustrating the principle involved in a two-electrode cell with direct gas access to a sensing electrode S and gas access to a counter electrode C via the sensing electrode S. The space between the two electrodes is occupied by a structure indicated generally as 10 which permits the passage of both electrolyte and gas between the two electrodes. As previously explained, any gas which reacts fully at the first or sensing electrode S will be removed and will therefore not pass across the intervening space 10 to the second electrode C. Accordingly, the electrode C will respond to any other gas which reacts only partially at the first electrode S. In this way it is possible to achieve partial or even complete elimination of the effect of an interfering gas as previously described. As shown in this simple explanatory view, the output signal of the cell is generated by passage of the cell current through a load resistor $R_L$ and appears across terminals 11, from where it can be amplified as required.

Figure 2:
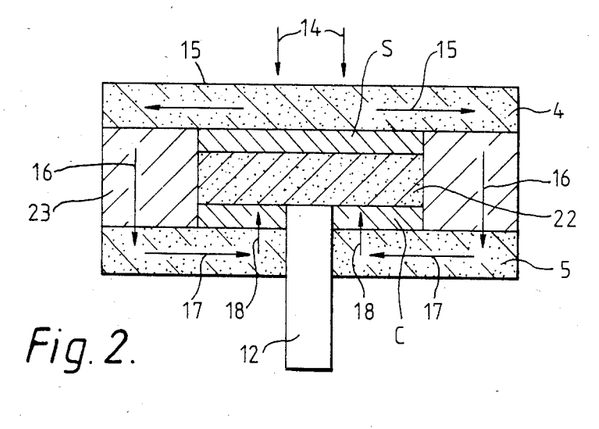
FIGS. 2 and 3 are schematic sectional views of a cell showing gas diffusion paths.
Figure 3:
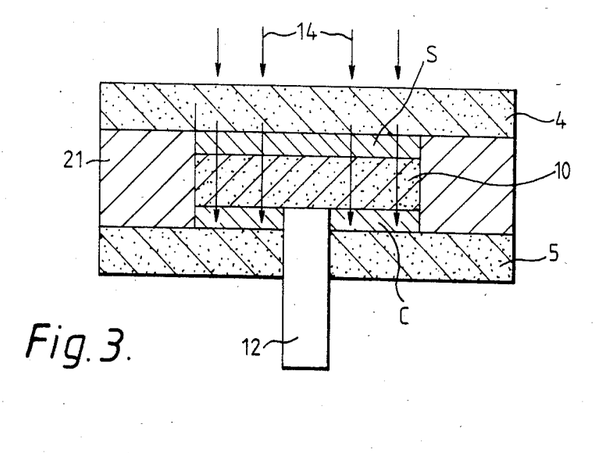

As just described, the structure 10 between the two electrodes needs to provide both a gas diffusion path between the two electrodes and also a path for the electrolyte and FIGS. 2 and 3 provide theoretical diagrammatic views of these two different types of path. In FIG. 2, the electrode S is shown mounted on a porous PTFE tape 4, and direct gas access to this electrode is indicated by arrows 14. The second electrode C is mounted on a porous PTFE tape 5 and the space between the two electrodes is occupied by a conventional hydrophilic separator 22 surrounded by a gasket 23 made of porous PTFE. The separator 22 is saturated with electrolyte drawn from a reservoir (not shown) by a hydrophilic wick 12 passing through a hole in the electrode C.

Gas impinging on the surface of the tape 4 can pass through this tape into contact with the electrode S and can also spread laterally as indicated by the arrows 15, after which it passes downwardly along the direction of the arrows 16 and then inwardly along the arrows 17 through the tape 5, finally passing into contact with the electrode C along the arrows 18. It will thus be seen that a central electrolyte path through the separator 22 is surrounded by a gas path through the gasket 23.

Although it is theoretically possible for the two separate paths to be concentrated in separate areas as illustrated in FIG. 2, it is preferable for the paths to be divided up into elements which are interspersed with one another as illustrated in FIG. 3, by the use of a partly hydrophobic, partly hydrophilic separator which is shown as 10 in order to equate it with the basic structure illustrated in FIG. 1. This takes the place of the hydrophilic separator 22 shown in FIG. 2 while the porous PTFE gasket 23 is replaced by a non-porous spacing gasket 21. Accordingly, both the gas and electrolyte paths are concentrated in the central area through the separator 10. Such a separator may be produced as a modification of known hydrophobic fuel cell electrodes in which a hydrophilic insulating material replaces the normal catalyst.

The separator can conveniently be made, for example, by impregnating glass filter paper with a mixed suspension of silica powder and PTFE powder, drying and curing at 300 degrees centigrade. This will result in a separator with a network of hydrophilic channels through which electrolyte can penetrate, interleaved with a network of hydrophobic channels available for gas permeation. Other separator materials may, of course, be used together with other hydrophobic and hydrophilic materials, to achieve the same effect. An alternative method of making a partly hydrophobic, partly hydrophilic separator is to simply impregnate a glass filter paper separator in a number of restricted areas with PTFE suspension and dry and cure as before. The impregnated areas will be hydrophobic and provide gas channels through the separator, and the unimpregnated areas are available to provide the electrolyte connection. Another form of the separator is a hydrophilic separator with a hole, or holes filled with porous hydrophobic material. By mounting such a separator in close contact with the first electrode on one side and with a second electrode on the other, there will be a gas path right through the hydrophobic channels of the first electrode and the separator into the second electrode.

Figure 4:
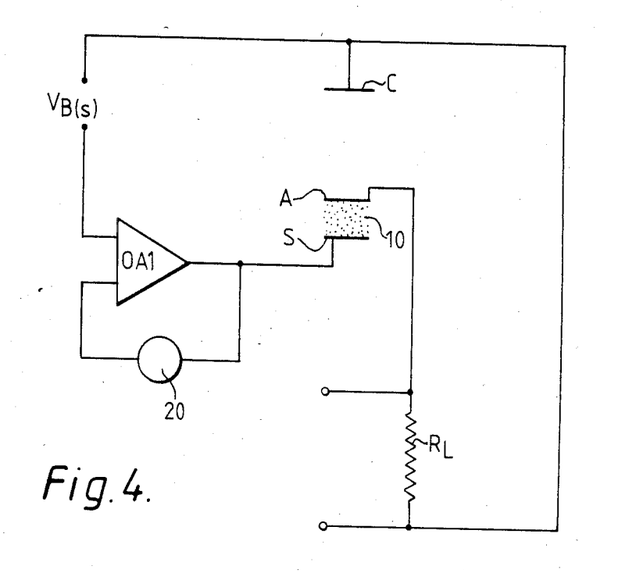
FIGS. 4 and 5 are circuit diagrams.

FIG. 4 illustrates a modification of the basic arrangement of the first three Figures, which includes an additional third electrode without gas access and spaced from the second electrode within the electolyte. This third electrode becomes the counter electrode indicated as C, the first two electrodes, between which the separator 10 is located, constituting a sensing electrode S and an auxiliary electrode A respectively. As previously described, such an arrangement renders it possible to filter out an interfering gas and obtain signals corresponding both to the interfering gas and to the gas of primary interest. In this arrangement, the electrode S has the primary access to the gas under test, access to the electrode A being by way of the separator 10 as previously described. The potential of the electrode S is set by a bias voltage $V_B(S)$ to the value required to ensure reaction of the interfering gas at the electrode S without excessive reaction of the gas of primary interest, which passes through the electrode S to be measured at the electrode A. The bias voltage $\bar{V}_B(S)$ is maintained constant by an operational amplifier OA1 and the current passing through the electrode S is measured by a current measuring device 20 to provide a measure of the concentration of the interfering gas. The gas of primary interest flowing from the electrode C flows through a resistor $R_L$ and the voltage measured across the ends of this resistor gives the concentration of the gas of primary interest.

Figure 5:
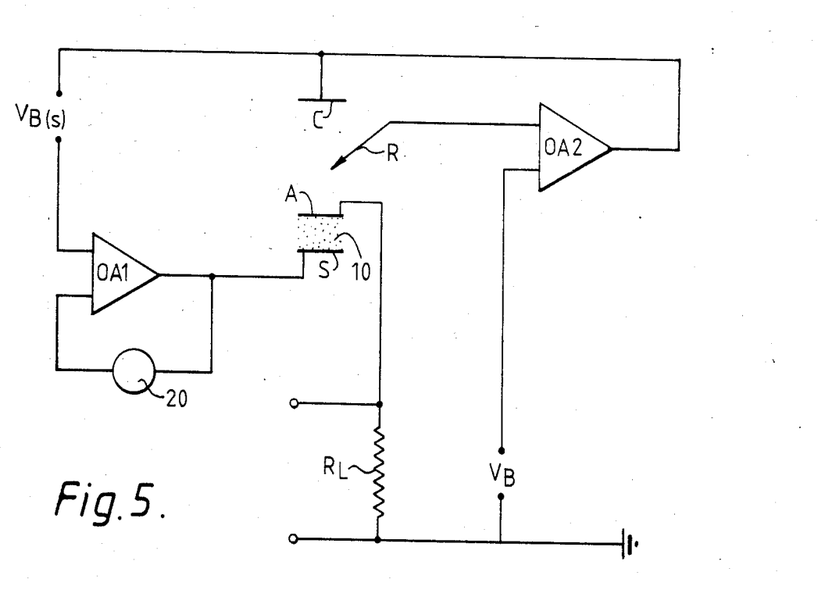

FIG. 5 shows a circuit similar to that of FIG. 4, but including an additional reference electrode R used in conjunction with a second operational amplifier OA2 and bias voltage $V_B$ to eliminate the effect of polarisation at the cathode and to apply a bias as will be described in more detail in conjunction with FIG. 8.

Figure 6:
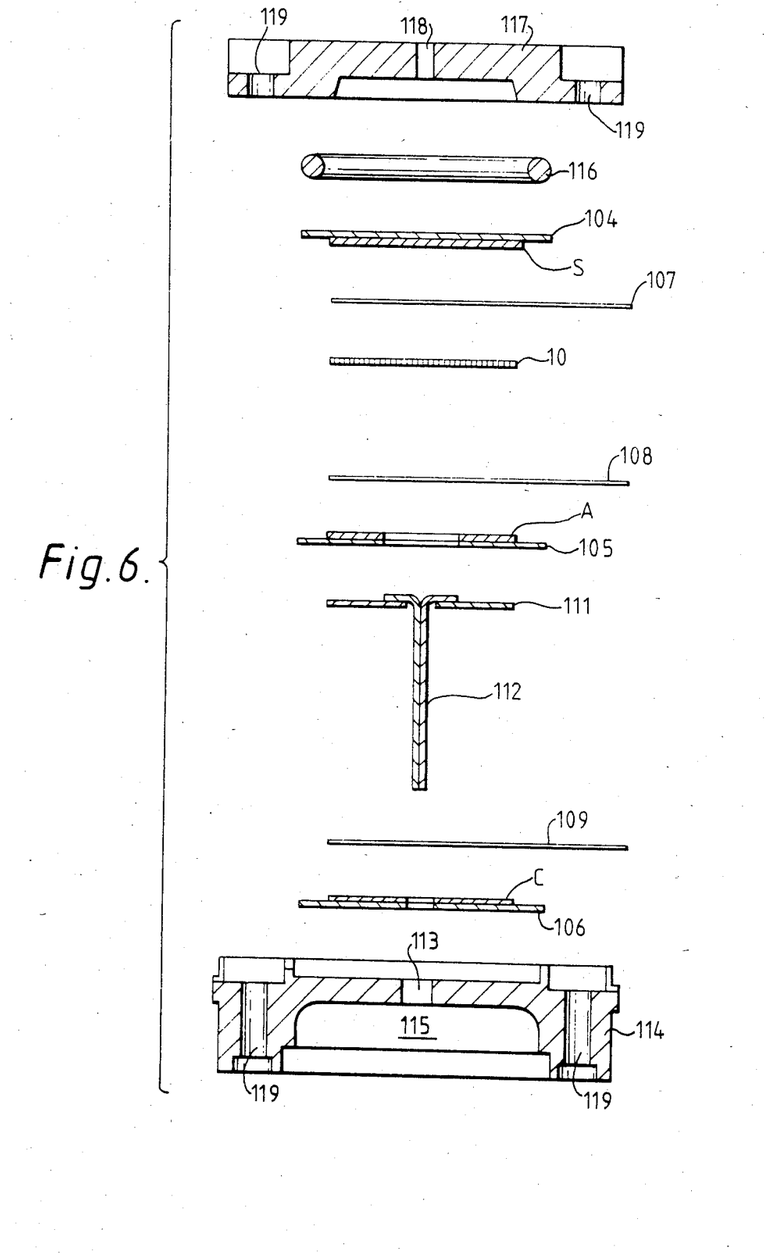
FIG. 6 is an exploded longitudinal sectional view of a compact sensor, which is suitable for use according to the invention.
Figure 7:
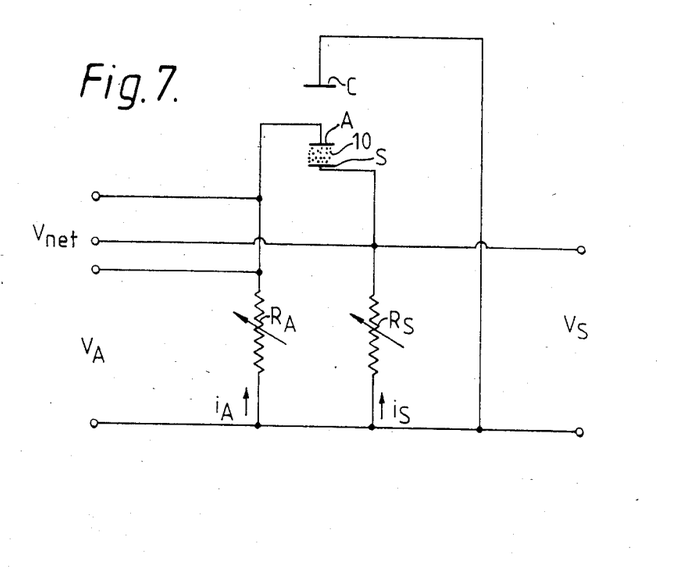
FIGS. 7 and 8 are further circuit diagrams.

The three-electrode arrangement of FIGS. 4 and 5 can be modified to operate in accordance with the subtractive principle as described in detail in our co-pending application Ser. No. 631,832 of even date herewith. The circuit details of such an arrangement are shown in FIGS. 7 and 8, and FIG. 6 shows details of the construction of a cell operating in this way.

The three electrodes S, A and C are hydrophobic type electrodes in which the electrode catalyst is mixed with powdered PTFE and pressure bonded to porous PTFE tape 104, 105 and 106, the auxiliary electrode A and the counter electrode having holes through their middles. The respective current connection leads to the electrodes are shown as 107, 108 and 109. As previously, the partly hydrophilic, partly hydrophobic porous insulating separator is shown as 10. Below the auxiliary electrode A is a conventional hydrophilic porous insulating separator 111 and a wick 112 of similar material which contacts the electrode S through the hole in the electrode A on PTFE tape 105 and passes through the holes in the separator 111, the counter electrode C on PTFE tape 106 and a hole 113 in a base plate 114 which provides an electrolyte reservoir 115.

The cell may be modified to operate in accordance with a circuit shown in FIG. 8 which includes an additional reference electrode and this may be included either above or below the counter electrode C. The other components necessary for completion of the cell include a compression 0-ring 116 and a top plate 117 formed with a capillary diffusion barrier 118. The sensor is assembled by bolting up, using bolts through holes in the base plate 114 and top plate 117, two of which holes are shown at 119. After assembly, the reservoir 115 is partially filled with electrolyte and sealed off with a bottom cap (not shown). The electrolyte will then wick up into the various separators and electrodes. The separator 10 will be in close contact on the one side with the sensing electrode S and on the other side with the auxiliary electrode A so that there is a gas path through the hydrophobic channels of the sensing electrode S and the separator 10 into the auxiliary electrode A.

Instead of the capillary gas barrier 118, other types of diffusion barrier can be included if required, e.g. a porous membrane, a diffusion barrier having pores which are sufficiently small as to allow gas diffusion through them to be in accordance with the Knudsen principle or a non-porous membrane.

As already described, the three electrode arrangement of FIG. 4 differs from the two electrode arrangement of FIG. 1 in that the second electrode which forms the counter electrode of FIG. 1 becomes an auxiliary electrode in the circuit of FIG. 4 and the third electrode becomes the counter electrode. Accordingly, if the three electrode cell of FIG. 6 is to be used in two electrode form, the electrode A becomes the counter electrode, and the counter electrode C is omitted together with its supporting tape 106 and its current connection lead 109.

Figure 8:
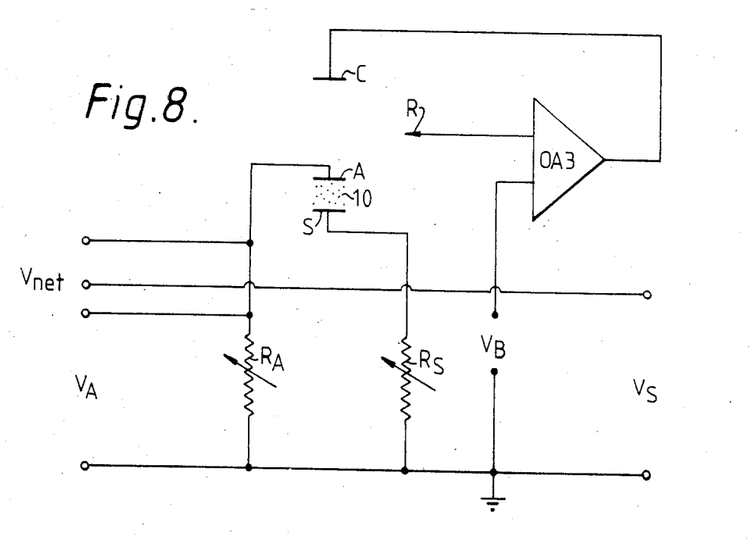

FIG. 7 is a circuit diagram illustrating the operation of the cell as shown in FIG. 6 and FIG. 8 is a corresponding diagram of the modified form of cell already referred to including an additional reference electrode. As shown in FIG. 7, the sensing electrode S and the auxiliary electrode A are connected in parallel each in series with a respective variable resistor $R_S, R_A$, the parallel arrangement being connected in circuit with the counter electrode C. If the currents flowing through the sensing and auxiliary electrodes respectively are denoted as $i_S$ and $i_A$, it will be seen that the output signal $V_{net}$ from the circuit will be given by $$V_{net} = i_S R_S - i_A R_A$$

As described, gas access is provided to the auxiliary electrode A via the sensing electrode S. Both the auxiliary and the sensing electrode will see a partially interfering gas so that its effect may be cancelled out. The two electrodes will be made as nearly identical as possible, but even so the signal from the interfering gas is liable to be lower on the auxiliary electrode than on the sensing electrode due to the longer diffusion path. The relative values of $R_A$ and $R_S$ may be adjusted to take account of this and so achieve substantially complete cancellation.

The circuit of FIG. 8 is similar but also includes an additional reference electrode R connected to a potential controlling operational amplifier OA3. If desired the circuit may also be used to apply a bias voltage $V_B$. The circuit will hold the potential between the reference electrode R and ground constant at the bias voltage $V_B$. It will be seen that the potential of the sensing electrode $V_S$ will now be given by $$V_S = V_R + V_B - i_S R_S$$

so that the potential of the sensing electrode is now independent of any potential changes at the counter electrode. In principle $V_B$ can be made positive, zero or negative and the sign of $i_S$ will depend on whether the sensing electrode is acting as an anode or a cathode. This circuit may be used both to cancel out the effect of a partially interfering gas and also to compensate for base line and any side effects from the residual potential change at the sensing electrode now equal to $i_S R_S$, as described in the co-pending application referred to above.

The following are some examples of sensors in accordance with the invention. In all these examples, the electrodes are gas diffusion electrodes of the hydrophobic type pressure bonded to porous PTFE tape, and the electrolyte is 10 normal sulphuric acid.

EXAMPLE 1

A two electrode sensor in accordance with the described modification of FIG. 6 had nominally identical platinum electrodes. The hydrophilic hydrophobic separator 10 was a glass mat separator with four hydrophobic channels, each of about 2 mm diameter made by impregnation with PTFE suspension and curing at 300 degrees centigrade, thus giving inter-electrode gas transmission as illustrated in FIG. 3. The sensor was fitted with a capillary diffusion barrier 118 consisting of three capillaries each of length 3 mm and diameter 1.7 mm. When tested using the circuit of FIG. 1 with a 47 ohm load resistor $R_L$, the signal generated by 100 ppm of carbon monoxide was 510 $\mu$V. A mixture of 100 ppm carbon monoxide and 100 ppm hydrogen gave 540 $\mu$V. A comparative conventional sensor, with a conventional hydrophilic separator and no gas access to the counter electrode via the sensing electrode gave, when tested on a mixture of 100 ppm carbon monoxide and 100 ppm hydrogen, a signal of 710 $\mu$V.

The comparison shows the significantly reduced interference from hydrogen by the use of gas transmission to the counter electrode via the sensing electrode according to the invention.

EXAMPLE 2

A sensor was made according to FIG. 6 but with an extra air reference electrode R, enabling it to be run with the circuit of FIG. 5 to produce a sensor for measuring hydrogen with insignificant interference from carbon monoxide and which also enabled carbon monoxide to be independently monitored. All the four electrodes contained platinum catalyst. The primarily exposed electrode S was biased at +350 mV relative to the air counter electrode C at which potential hydrogen reaction was relatively small.

Gas access via electrode S to electrode A was achieved using an annular gasket of porous PTFE according to FIG. 2. Electrode A was controlled by operational amplifier OA2 at substantially the same potential as the reference electrode R. The sensor was fitted with a capillary diffusion barrier 118, 3 mm long and 2.0 mm diameter.

When tested with mixtures of carbon monoxide and hydrogen in air, it was found that the signal taken off $R_L$ was virtually independent of the carbon monoxide concentration (100 ppm carbon monoxide <1 ppm hydrogen equivalent), but was linear with hydrogen concentration when tested between 0 and 100 ppm hydrogen. The current sensitivity to hydrogen was 0.018 μA per ppm. A signal corresponding to carbon monoxide was monitored by current measuring device 20 showing a sensitivity of 0.098 μA per ppm of carbon monoxide. This signal was slightly affected by hydrogen (100 ppm hydrogen gave 5 ppm carbon monoxide equivalent).

EXAMPLE 3

A sensor designed to measure carbon monoxide with insignificant interference from hydrogen was constructed as illustrated in FIG. 6. The separator 10 was made by totally impregnating a glass mat with a suspension of PTFE silica in equal weights, followed by drying and curing at 300 degrees centigrade. The sensor was used in conjunction with the circuit of FIG. 7.

When tested with hydrogen in air in a simulated conventional two electrode mode, i.e. with the signal taken across $R_S$ to measure the current between electrodes S and C, the hydrogen interference at 20 degrees centigrade was found to be 100 ppm of hydrogen equivalent to 40 ppm of carbon monoxide.

When run in the subtractive mode with the circuit according to FIG. 7, with $V_{net}$ used as the signal, it was found that the hydrogen interference could be reduced to zero by setting the ratio of $R_A:R_S$ to 1.6. Using $V_{net}$ as the signal the carbon monoxide sensitivity was equivalent to 0.12 μA per ppm.

Hydrogen could be monitored separately by taking a signal across $R_A$. Tested over the range 0–100 ppm the response was linear with a sensitivity of 0.034 μA per ppm.

We claim:

1. An electro-chemical gas sensor capable of sensing a gas of primary interest in the presence of an interfering gas, said sensor comprising a housing, an electrolyte contained within said housing, first and second hydrophobic gas diffusion electrodes permeable to gas contacting said electrolyte, means for measuring the current passing between said first and second electrodes, each of said first and second electrodes comprising a powdered catalyst, a hydrophobic plastic material bonding said catalyst and a porous hydrophobic plastic support means, first means defining a first gas path, said first gas path providing gas access to said first electrode, and second means within said housing defining second and third porous insulating paths between said first and second electrodes, said second path means being hydrophilic and providing an electrolyte path between said first and second electrodes, said third path being hydrophobic and impermeable to electrolyte but permeable to gas and providing a path for diffusion of gas from said first electrode to said second electrode such that said third path provides access from said first electrode to said second electrode for interfering gas that has not fully reacted at said first electrode.

2. A gas sensor according to claim 1, in which the arrangement of said first and second electrodes and said second means for providing said second gas path is such that gas reaching said second electrode must first pass through said first electrode.

3. A gas sensor according to claim 2, in which said second means for providing said second gas path includes between said first and second electrodes a porous insulating separator, said separator being partly hydrophilic and partly hydrophobic, thus providing a path for gas while preserving an electrolyte path between said first and second electrodes.

4. A gas sensor according to claim 3, in which said separator comprises a network of hydrophilic channels through which electrolyte can penetrate, interspersed with a network of hydrophobic channels for gas permeation.

5. A gas sensor according to claim 4, in which said separator comprises contiguous hydrophilic and hydrophobic areas.

6. A gas sensor according to claim 1, which includes an additional third electrode, said third electrode being spaced from said second electrode and in contact therewith via said electrolyte, said third electrode functioning as a common counter electrode to said first and second electrodes, said first electrode being selected so as to react fully with an interferring gas and at most partially with a gas of primary interest and said second electrode being selected so as to react with said gas of primary interest, whereby current flowing between said first and second electrodes provides a measure of said interferring gas and the current flowing between said second and third electrodes provides a measure of said gas of primary interest, and means for measuring said currents.

7. A gas sensor according to claim 6, further including a reference electrode located adjacent said third electrode and within said electrolyte, and a potentiostatic circuit connected to said reference electrode to control the potential of said second electrode.

8. A gas sensor according to claim 6, further including two separate potentiostatic circuits to independently control the potentials of both of said first and second electrodes in relation to said third electrode.

9. A gas sensor according to claim 1, further includes a reference electrode in contact with said electrolyte, and a potentiostatic circuit connected to said reference electrode to control the potential of said first electrode.

10. A gas sensor according to claim 1, further comprising a diffusion barrier controlling access of the gas being sensed to said first electrode.

11. A gas sensor according to claim 10, wherein said diffusion barrier is selected from the group comprising a capillary, a porous membrane, a diffusion barrier having pores which are sufficiently small as to allow gas diffusion through them to be in accordance with the Knudsen principle, and a nonporous membrane.

12. A gas sensor according to claim 1, in which the arrangement of said first and second electrodes and said second means for providing said second and third gas path is such that gas reaching said second electrode must first pass around said first electrode.

13. A gas sensor according to claim 1, in which said hydrophobic plastic is a fluorocarbon.

14. A gas sensor according to claim 1, which includes an additional third electrode, said third electrode being spaced from said second electrode and in contact with said electrolyte, said third electrode functioning as a common counter electrode to said first and second electrodes, said first electrode being selected so as to react fully with a gas of primary interest and at most partially with an interfering gas and said second electrode being selected so as to react with said interfering gas, whereby current flowing between said first and third electrodes provides a measure of said gas of primary interest and the current flowing between said second and third electrodes provides a measure of said interfering gas, and means for measuring said currents.

15. A gas sensor according to claim 1, which includes an additional third electrode, said third electrode being spaced from said second electrode and in contact with said electrolyte, said third electrode functioning as a common counter-electrode to said first and second electrodes, whereby, in operation, respective currents flow between said first and third electrodes and between said second and third electrodes, electric circuit means for subtracting a predetermined fraction or multiple of the current passing through said second electrode from the current passing through said first electrode, and means for measuring the resulting net current to provide an output signal.

* * * * *

UNITED STATES PATENT AND TRADEMARK OFFICE
CERTIFICATE OF CORRECTION

PATENT NO. : 4,587,003
DATED : May 6, 1986
INVENTOR(S) : Anthony D.S. Tantram; Yat S. Chan It is certified that error appears in the above-identified patent and that said Letters Patent is hereby corrected as shown below:

In Column 4, Line 37, after "interfering gas.", cancel "The gas of primary interest flowing from the electrode C flows through a resistor $R_L$", and insert therefore --The current passing through the electrode A flows through a resistor $R_L$--.

Signed and Sealed this

Thirteenth Day of March, 1990

Attest:

JEFFREY M. SAMUELS

*Attesting Officer*    Acting Commissioner of Patents and Trademarks